United States Patent
Zhan et al.

(10) Patent No.: US 10,092,198 B2
(45) Date of Patent: Oct. 9, 2018

(54) MEDICAL PENDANT SYSTEM

(71) Applicant: Maquet (Suzhou) Co. Ltd., Suzhou (CN)

(72) Inventors: Shengping Zhan, Suzhou (CN); Wei Zhang, Suzhou (CN); Jiasheng Huang, Suzhou (CN); Qunhua Li, Suzhou (CN); Ming Ji, Suzhou (CN)

(73) Assignee: Maquet (Suzhou) Co. Ltd., Suzhou (CN)

(*) Notice: Subject to any disclaimer, the term of this patent is extended or adjusted under 35 U.S.C. 154(b) by 341 days.

(21) Appl. No.: 14/899,777

(22) PCT Filed: Jun. 10, 2014

(86) PCT No.: PCT/CN2014/079571
§ 371 (c)(1),
(2) Date: Dec. 18, 2015

(87) PCT Pub. No.: WO2014/201960
PCT Pub. Date: Dec. 24, 2014

(65) Prior Publication Data
US 2016/0143550 A1    May 26, 2016

(30) Foreign Application Priority Data

Jun. 19, 2013  (CN) .......................... 2013 1 0242880
Apr. 30, 2014  (CN) .......................... 2014 1 0181033

(51) Int. Cl.
*A61B 5/024*     (2006.01)
*E04F 17/08*     (2006.01)
(Continued)

(52) U.S. Cl.
CPC ........ *A61B 5/02438* (2013.01); *A61B 5/6802* (2013.01); *A61B 5/742* (2013.01);
(Continued)

(58) Field of Classification Search
CPC .... A61B 5/02438; A61B 5/6802; A61B 5/742
(Continued)

(56) References Cited

U.S. PATENT DOCUMENTS

| 5,625,537 A | 4/1997 | Neuder |
| 7,073,765 B2 | 7/2006 | Newkirk |

(Continued)

FOREIGN PATENT DOCUMENTS

| CN | 102198034 A | 9/2011 |
| CN | 103294070 A | 9/2013 |

(Continued)

OTHER PUBLICATIONS

Intellectual Property Office of Singapore, Search Report, Application No. 11201510401V, dated Aug. 31, 2016.
(Continued)

*Primary Examiner* — Thomas Skibinski
(74) *Attorney, Agent, or Firm* — Quarles & Brady LLP (57) ABSTRACT

A medical pendant system, comprising: a movable component, an execution component and a bus (1); the movable component comprises a key control module (3); the key control module (3) comprises a braking system control key (K1, K4) and a pendant lifting/lowering control key (K2, K3); the execution component comprises an output control part (4), the output control part (4) being connected respectively with a bus power supply (5), a pendant motor (9) and a braking system (10); the movable component and the execution component are connected respectively to the bus (1); the bus (1) is used for transmitting power supply and also for transmitting instructions from the movable component to the execution component. In the vertical direction the medical pendant system can be adjusted steplessly without having to alter the lengths of the cables. The number of cable cores is reduced, circuit design is optimized, installation and (Continued)

maintenance are easy, functional integration and extension are convenient, and reliability is improved.

11 Claims, 5 Drawing Sheets

(51) Int. Cl.
 *A61B 5/00* (2006.01)
 *H01H 47/00* (2006.01)
 *A61G 12/00* (2006.01)
(52) U.S. Cl.
 CPC .............. *E04F 17/08* (2013.01); *H01H 47/00* (2013.01); *A61G 12/002* (2013.01)
(58) Field of Classification Search
 USPC ......... 307/115; 700/275; 361/624, 825, 775; 248/317
 See application file for complete search history.

(56) References Cited

U.S. PATENT DOCUMENTS

| | | | |
|---|---|---|---|
| 7,770,860 B1 | 8/2010 | Culpepper et al. | |
| 2009/0201632 A1* | 8/2009 | Bauer | H02G 3/0493 361/624 |
| 2011/0118879 A1* | 5/2011 | Bauer | A61G 12/002 700/275 |

FOREIGN PATENT DOCUMENTS

| | | |
|---|---|---|
| CN | 203299653 U | 11/2013 |
| CN | 103591425 A | 2/2014 |
| DE | 102009009549 A1 | 9/2010 |
| EP | 1424755 A1 | 6/2004 |
| EP | 1690517 A2 | 8/2006 |
| EP | 2322130 A1 | 5/2011 |
| EP | 2455053 A1 | 5/2012 |
| JP | S63022088 U1 | 2/1988 |
| JP | S63022088 Y | 6/1988 |
| JP | H04131886 U1 | 12/1992 |
| JP | 2008251504 A | 10/2008 |
| JP | 2010507202 A | 3/2010 |
| JP | 2012130801 A | 7/2012 |
| WO | 2013074800 A1 | 5/2013 |

OTHER PUBLICATIONS

Intellectual Property Office of Singapore, Written Opinion, Application No. 11201510401V, dated Aug. 31, 2016.
Japan Patent Office, Notice of Reasons for Rejection, Application No. 2016-520257, dated Oct. 24, 2016.
PCT International Search Report, PCT/CN2014/079571, dated Sep. 2, 2014, 4 pages.
European Patent Office, Extended European Search Report, Application No. 14813742.5, dated Jan. 20, 2017.
European Patent Office, Communication pursuant to Article 94(3) EPC for corresponding EP Application No. 14813742.5, dated Nov. 3, 2017, 7 pages.
European Patent Office, Communication pursuant to Article 94(3) EPC for corresponding EP Application No. 14813742.5, dated Jun. 28, 2018, 6 pages.

* cited by examiner

MEDICAL PENDANT SYSTEM

CROSS-REFERENCE TO RELATED APPLICATIONS

The present application represents the national stage entry of PCT International Patent Application No. PCT/CN2014/079571 filed on Jun. 10, 2014, which claims priority of Chinese patent application No. 201310242880.9 filed on Jun. 19, 2013 and Chinese patent application No. 201410181033.0 filed on Apr. 30, 2014, the disclosures of which are incorporated herein by reference for all purposes.

TECHNICAL FIELD

The present invention relates to the technical field of medical equipment, and more particularly to a medical pendant system.

BACKGROUND ART

Figure 1:
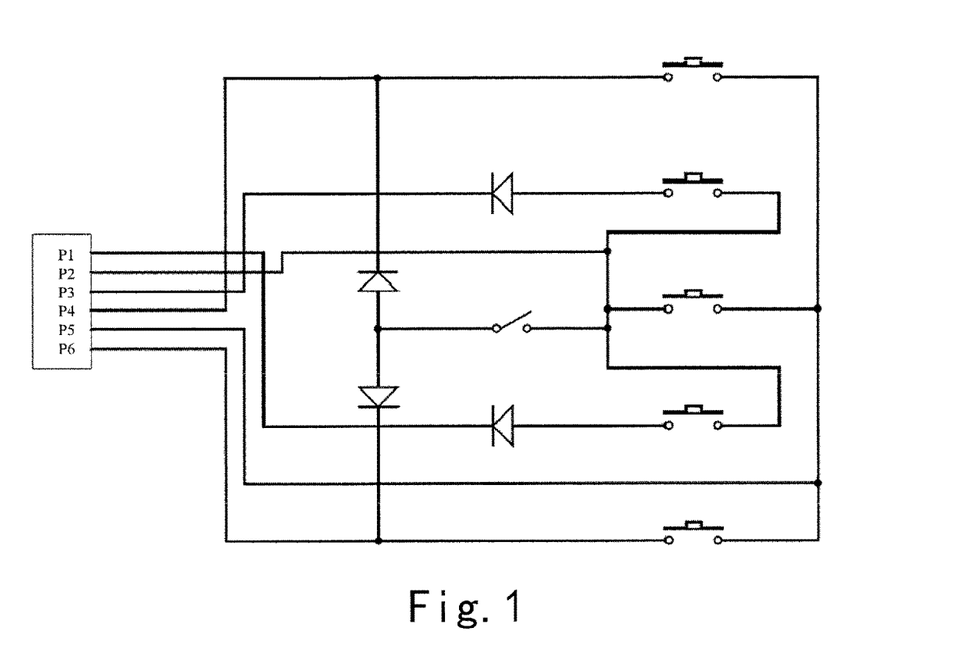
FIG. 1 is a line diagram for the key control end of the medical pendant system of the prior art.

Medical pendant system is an indispensable medical equipment used in modern hospital operating room, intensive care unit and the like. The current medical pendant systems mainly employ the following technical solutions: the circuit control part is connected in a fixed position manner; the line control part is connected in one-to-one manner; the number of several control keys corresponding to the number of several loops, see FIG. 1; and different main control circuits corresponding to different applications.

Disadvantages of such technical solutions are: the location adjustment is not convenient for the users; there are too many cables, the space occupancy is relatively high, and the length of the cables is fixed; there are no extended functions; the maintenance is not convenient; and there are too many main control circuit boards, leading not versatile.

SUMMARY OF INVENTION

The purpose of the present invention is to overcome the above-mentioned disadvantages of the existing medical pendant systems, in the vertical direction the medical pendant system can be adjusted steplessly without having to alter the lengths of the cables; the number of cable cores is reduced, circuit design is optimized, installation and maintenance are easy, functional integration and extension are convenient, and reliability is improved.

The above purpose of the present invention is achieved by a medical pendant system, wherein the medical pendant system comprises a movable component, an execution component and a bus; the movable component comprises a key control module; the key control module comprises a braking system control key and a pendant lifting/lowering control key; the execution component comprises an output control part; the output control part is connected respectively with a bus power supply, a pendant motor, and a braking system; the movable component and the execution component are connected respectively to the bus; the bus is used for transmitting power supply, and also used for transmitting instructions from the movable component to the execution component.

According to the technical solution described above, the medical pendant system of the present invention can have the following beneficial technical effects: in the vertical direction the medical pendant system can be adjusted steplessly without having to alter the lengths of the cables; the number of cable cores is reduced, circuit design is optimized, installation and maintenance are easy, functional integration and extension are convenient, and reliability is improved.

Preferably, the medical pendant system further comprises a relay module located between the movable component and the bus, and a relay module located between the execution component and the bus.

According to the technical solution described above, the medical pendant system of the present invention can have the following beneficial technical effects: the electrical connection and the mechanical connection among the movable component, the execution component and the bus can be achieved, various modules having control function or data transfer function are connected into the bus, and the individual modules can be ensured to be steplessly adjusted in lengthwise direction.

Preferably, the bus is disposed in an inner groove inside the pendent cabinet or on the exterior surface thereof and extending along the lengthwise direction of the pendant cabinet, and the bus comprises an insulator accommodated inside the inner groove, and a conductor enclosed inside the insulator.

According to the technical solution described above, the medical pendant system of the present invention can have the following beneficial technical effects: it can possess a standardized interface, without complicatedly connecting electrical cables, disassembly is easy, and the free adjustment of the position of a medical attachment is allowed.

Preferably, the inner groove is substantially filled when the insulator is accommodated inside the inner groove and the conductor is enclosed inside the insulator.

According to the technical solution described above, the medical pendant system of the present invention can have the following beneficial technical effects: the electrical interface has good reliability and insulation performance, effectively preventing the infiltration of water or other cleaning agents during the cleaning process in a hospital.

Preferably, the number of lines of the bus is two, namely, the bus comprises two insulators accommodated inside the inner groove and two conductors respectively enclosed inside the two insulators.

According to the technical solution described above, the medical pendant system of the present invention can have the following beneficial technical effects: by means of the appropriate number and settings of the above insulators and conductors, a simple and reliable connection between the pin of the relay module and the conductor inside the cabinet can be achieved.

Preferably, the cross section of the conductor is substantially Y-shaped, $\Omega$-shaped, V-shaped, W-shaped, C-shaped, or T-shaped.

According to the technical solution described above, the medical pendant system of the present invention can have the following beneficial technical effects: by means of the appropriate shape of the above conductor, a simpler and reliable connection between the pin of the relay module and the conductor inside the cabinet can be achieved.

Preferably, the output control part is further connected with a pendant protecting sensor.

According to the technical solution described above, the medical pendant system of the present invention can have the following beneficial technical effects: an effective connection between the pendant and other medical devices can be ensured before lifting and lowering by the motor, thus working normally.

Preferably, the output control part is further connected with a height limiting unit for limiting the lifting and lowering range of the pendant.

According to the technical solution described above, the medical pendant system of the present invention can have the following beneficial technical effects: providing the limitation for the range for lifting and lowering the pendant system.

Preferably, the output control part is further connected with a pendant motor power supply.

According to the technical solution described above, the medical pendant system of the present invention can have the following beneficial technical effects: the pendant motor power supply can be provided to supply power to the pendant motor.

Preferably, the movable component further comprises an environmental lamp module.

According to the technical solution described above, the medical pendant system of the present invention can have the following beneficial technical effects: it can conveniently provide environmental illumination.

Preferably, the movable component further comprises a display module, the execution component further comprises a display data line module.

According to the technical solution described above, the medical pendant system of the present invention can have the following beneficial technical effects: a display can be conveniently connected.

Preferably, the movable component further comprises a pulse sensor module, the execution component further comprises a pulse diagnostic instrument module.

According to the technical solution described above, the medical pendant system of the present invention can have the following beneficial technical effects: a pulse sensor and a pulse diagnostic instrument can be conveniently connected.

Preferably, the key control module further comprises an input conversion interface.

According to the technical solution described above, the medical pendant system of the present invention can have the following beneficial technical effects: the conversion of key instructions into instructions which are recognizable by a bus transmission can be realized.

The above purpose of the present invention is further achieved by a medical pendant system, wherein the medical pendant system comprises a movable component, an execution component and a bus; the movable component comprises a key control module; the key control module comprises a braking system control key and a pendant lifting/lowering control key; the execution component comprises an output control part; the output control part is connected respectively with a bus power supply, a pendant motor, and a braking system; the movable component and the execution component are connected respectively to the bus; the medical pendant system further comprises a relay module located between the movable component and the bus, and a relay module located between the execution component and the bus, the two relay modules are substantially identical and both of them comprise a relay module mechanical interface and a relay module electrical interface for respectively connecting to a cabinet mechanical interface and a cabinet electrical interface disposed on the pendant cabinet.

According to the technical solution described above, the medical pendant system of the present invention can have the following beneficial technical effects: in the vertical direction the medical pendant system can be adjusted steplessly without having to alter the lengths of the cables; the number of cable cores is reduced, circuit design is optimized, installation and maintenance are easy, functional integration and extension are convenient, and reliability is improved.

Preferably, the relay module mechanical interface comprises a concave curved surface portion or a convex curved surface portion disposed on the relay module, and the cabinet mechanical interface comprises correspondingly a convex curved surface portion or a concave curved surface portion disposed on the pendant cabinet.

According to the technical solution described above, the medical pendant system of the present invention can have the following beneficial technical effects: the mechanical connection can be effectively achieved and the connection reliability is improved; furthermore, a medical attachment is easy to be disassembled and the position of the medical attachment can be freely and steplessly adjusted.

Preferably, the relay module electrical interface comprises a pin disposed on the relay module, and the cabinet electrical interface comprises the bus disposed on the pendant cabinet.

According to the technical solution described above, the medical pendant system of the present invention can have the following beneficial technical effects: it can possess a standardized electrical interface, without complicatedly connecting electrical cables, disassembly is easy, and the free adjustment of the position of a medical attachment is allowed.

LIST FOR REFERENCE NUMERALS 1. bus;
2. environmental lamp module;
3. key control module;
4. output control part;
5. bus power supply;
6. pendant protecting sensor;

7. pendant motor power supply;
8. height limiting unit;
9. pendant motor;
10. braking system;
11. display module;
12. display data line module;
13. pulse sensor module;
14. pulse diagnostic instrument module;
15. relay module;
16. pendant cabinet;
17. conductor;
18. insulator;
31. input conversion interface;
100. handle;
151. relay module mechanical interface;
152. relay module electrical interface;
161. cabinet mechanical interface;
162. inner groove;
200. laminate;
K1. braking system control key;
K2. pendant lifting/lowering control key;
K3. pendant lifting/lowering control key;
K4. braking system control key.

DETAILED DESCRIPTION

The present invention is further described in connection with drawings and particular embodiments as follows and elaborated in more detail in the following description in order to fully understand the present invention, but it is evident that the present invention can be implemented in many other ways which are different from those described herein; generalization and deduction can be made by a skilled in the art without departing from the connotation of the invention according to practical application, and therefore the protective scope of the present invention should not be limited by the specific content of embodiments of the present invention herein.

Figure 2:
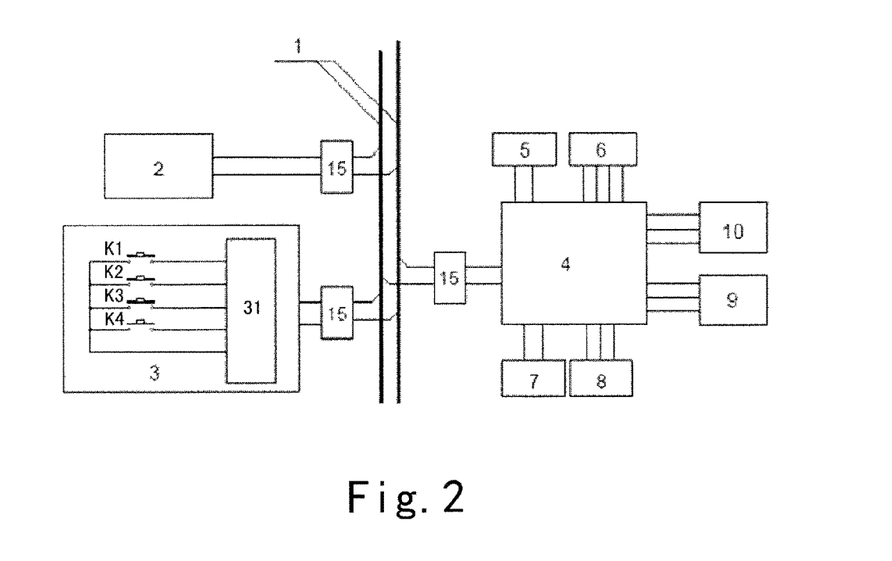
FIG. 2 is a line diagram for the medical pendant system of an embodiment of the present invention.

FIG. 2 shows a line diagram for the medical pendant system of an embodiment of the present invention.

The medical pendant system of the present invention comprises a movable component, an execution component and a bus 1; the movable component comprises a key control module 3; the key control module 3 comprises a braking system control keys K1 and K4 and a pendant lifting/lowering control keys K2 and K3; the execution component comprises an output control part 4; the output control part 4 is connected respectively with a bus power supply 5, a pendant motor 9, and a braking system 10; the movable component and the execution component are connected respectively to the bus 1; and the bus 1 is used for transmitting power supply, and also used for transmitting instructions from the movable component to the execution component.

The present invention employs power supply carrier wave technology, utilizes two conductors as bus carrier, which in one aspect is used for transmitting the power supply, and in another aspect is used for transmitting instructions (i.e., transmitting instructions from the movable component to the execution component), thus achieving the control of the output control part 4 via the key control module 3, and then driving the execution component by means of the output control part 4.

Preferably, the key control module 3 of the present invention comprises a key control part and an input conversion interface 31, wherein the two parts are designed integrally for achieving the operation of the basic functions. The key comprises the braking system control keys K1 and K4, as well as the pendant lifting/lowering control keys K2 and K3. The input conversion interface 31 is used for converting the key instructions into instructions which are recognizable by bus transmission. The number of the key control module 3 in the medical pendant system is not limited to one, and more than one key control modules can be used (considering that the key control modules are likely installed on all of the different sides for the convenient spot operation).

Preferably, the output control part of the present invention can be used for achieving the conversion of the instructions on the bus into the instructions which are recognizable by the execution component, thereby ensuring that the system achieves the control action on various execution components via the bus.

Preferably, as shown in FIG. 2, the number of the output control part is one. In this way, since power supply carrier wave technology is employed and two conductors are used as bus carrier, multiple execution components such as the pendant motor and the braking system can be controlled by only one output control part, and the control can further extend to such execution components as the pendant protecting sensor, the height limiting unit, the pendant motor power supply, or the environmental lamp module or the like.

Certainly, on the basis of the present invention, a person skilled in the art should understand that the number of the output control part of the present invention is not limited to one, other numbers such as two, three can also be used. Various numbers of the output control parts fall into the protective scope of the present invention, so long as the effective control of multiple execution components can be achieved.

Preferably, as shown in FIG. 2, the medical pendant system further comprises a relay module 15 located between the movable component and the bus 1, and a relay module 15 located between the execution component and the bus 1.

Preferably, as shown in FIG. 2, the output control part 4 is further connected with a pendant protecting sensor 6.

Preferably, as shown in FIG. 2, the output control part 4 is further connected with a height limiting unit 8 for limiting the lifting and lowering range of the pendant.

Preferably, as shown in the FIG. 2, the output control part 4 is further connected with a pendant motor power supply 7.

Preferably, as shown in FIG. 2, the movable component further comprises an environmental lamp module 2. The environmental lamp module 2 can be an integrated module or a split module.

That is to say, in addition to the bus power supply, the pendant motor and the braking system, a person skilled in the art should understand, on the basis of the present invention, that the movable component can further be extended, for example, to include the pendant protecting sensor 6, the height limiting unit 8, the pendant motor power supply 7, or the environmental lamp module 2.

The relevant modules or components which are possibly employed in the medical pendant system of present invention are presented in more details hereinafter.

Key control module 3: the statuses (pressed or released) of the four keys in its key part are respectively represented by different software codes; when the input conversion interface 31 receives a corresponding identification code, the identification code is converted into a bus instruction to be executed, with the identification of the code here directed against a single key; and if more than one keys are pressed at the same time, then no instruction is sent.

Relay module 15: it is used for the electrical connection and the mechanical connection, various modules having control function or data transfer function are connected into the bus, and the positions of the individual modules can be ensured to be fixed after they are moved in lengthwise direction.

Bus 1: it is used as a carrier for transmitting instructions to the output control part, and in another aspect, for achieving the electrical connection with the power supply.

Output control part 4: the output control part 4 will periodically scan to determine that whether there is an instruction sent from the bus 1, the matched instructions when received are converted into control instructions so as to drive the action of the corresponding execution component.

Bus power supply 5 (alternative/direct current power supply): it is used for providing control power supply for the bus system (the medical pendant system), in one aspect used for providing power supply for the bus system, and in another aspect used for providing power for the spot environmental lamp or other units.

Pendant protecting sensor 6: it is used for satisfying the requirements for protecting the pendant system under different applications; a set of corresponding instructions will be provided for the output control part when the pendant protecting sensor 6 senses a corresponding object; the output control part when receives the corresponding instructions will logically analyze the instructions correspondingly to produce corresponding output so as to make the pendant be capable of working normally.

Braking system 10: the system releases the corresponding shaft brake when the key K1 or K4 is pressed; and the system lock the corresponding shaft brake when the key K1 or K4 is released.

Pendant motor 9: it is used for driving the lifting or the lowering of the pendant. The pendant is lifted when the key K2 is pressed; and the pendant is lowered when the key K3 is pressed.

Height limiting unit 8: it is used for providing the limitation for the lifting and lowering range of the pendant. When the highest point set for the pendant is achieved, a set of corresponding instructions will be provided for the output control part to cease the continued lifting of the pendant, and the pendant in this case can only be lowered. When the lowest point set for the pendant is achieved, a set of corresponding instructions will be provided for the output control part to cease the continued lowering of the pendant, and the pendant in this case can only be lifted.

Pendant motor power supply 7: the pendant motor power supply 7 is disposed to supply power to the pendant motor.

Figure 3:
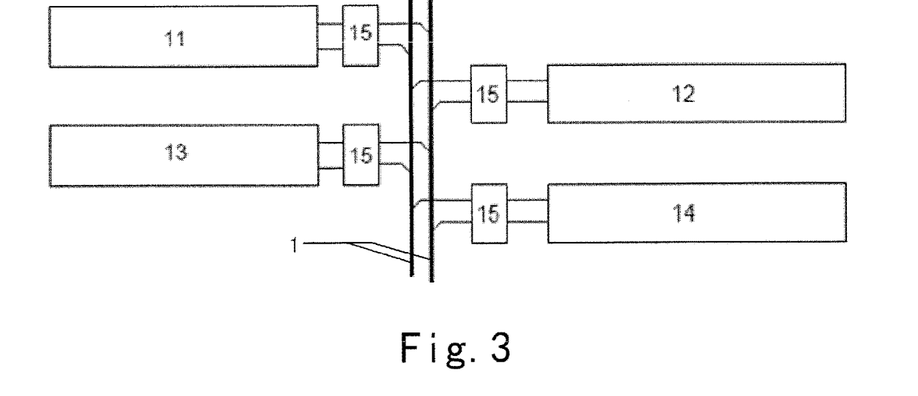
FIG. 3 is a functional extension line diagram for the medical pendant system of an embodiment of the present invention.

FIG. 3 shows a line diagram for functional extension of the medical pendant system of an embodiment of the present invention.

The bus is employed as a carrier to code, decode and convert video signals, audio signals, and pulse signals, thus achieving the connection and signal transmission of the pulse diagnostic instrument or the medical display and other extension devices.

Preferably, as shown in FIG. 3, the movable component further comprises a display module 11, and the execution component further comprises a display data line module 12. Note that the display module described here can include a display and a conversion interface, and the display data line module described here can include a display data line and a conversion interface.

Preferably, as shown in FIG. 3, the movable component further comprises a pulse sensor module 13, the execution component further comprises a pulse diagnostic instrument module 14. Note that the pulse sensor module described here can include a pulse sensor and a conversion interface, and the pulse diagnostic instrument module described here can include a diagnostic instrument and a conversion interface.

Figure 4:
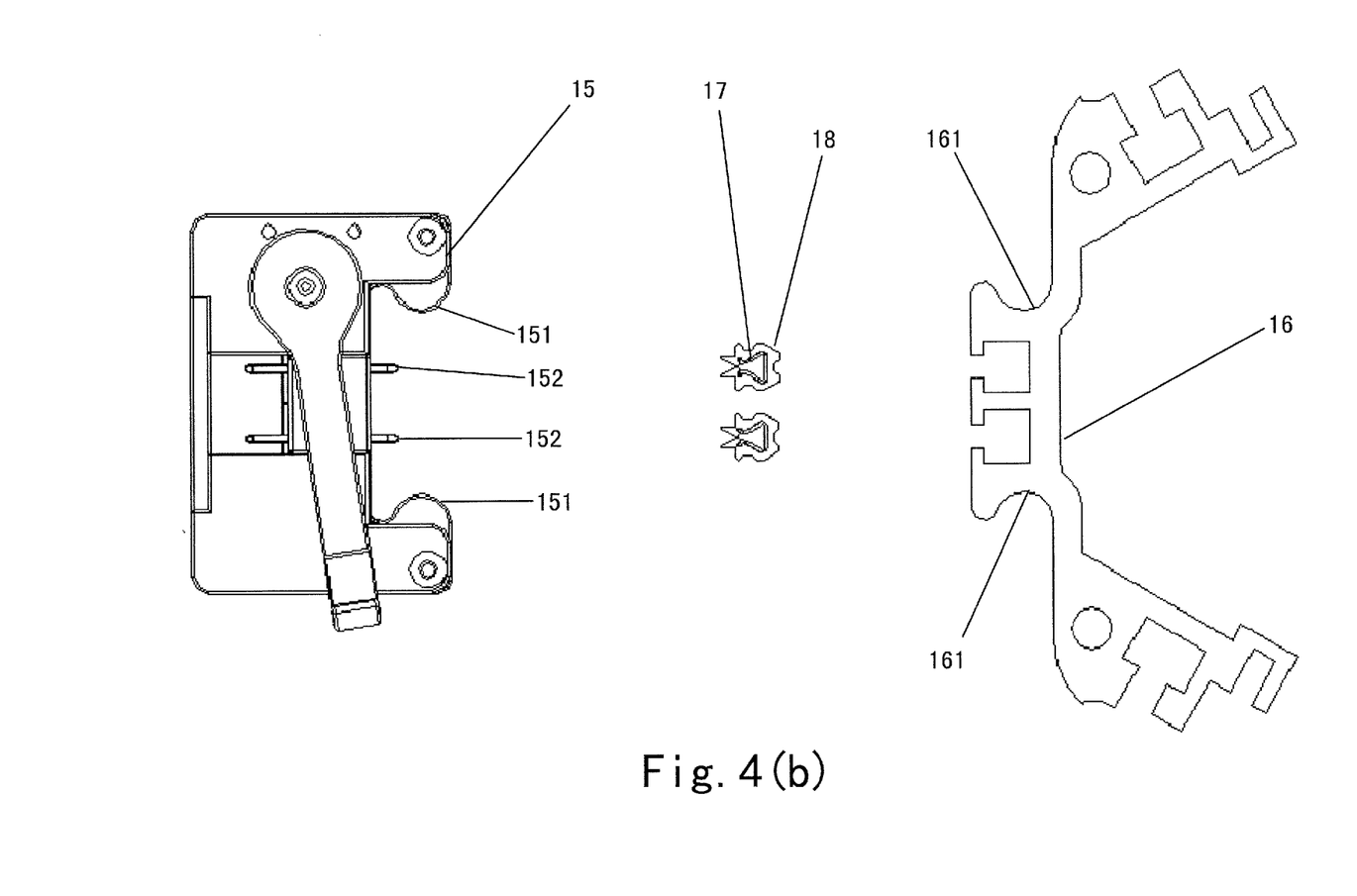
FIG. 4(a) is an exploded three-dimensional view for the relay module, bus and pendant cabinet of an embodiment of the present invention.
FIG. 4(b) is an exploded top view for the relay module, bus and pendant cabinet of an embodiment of the present invention.
Figure 4A:
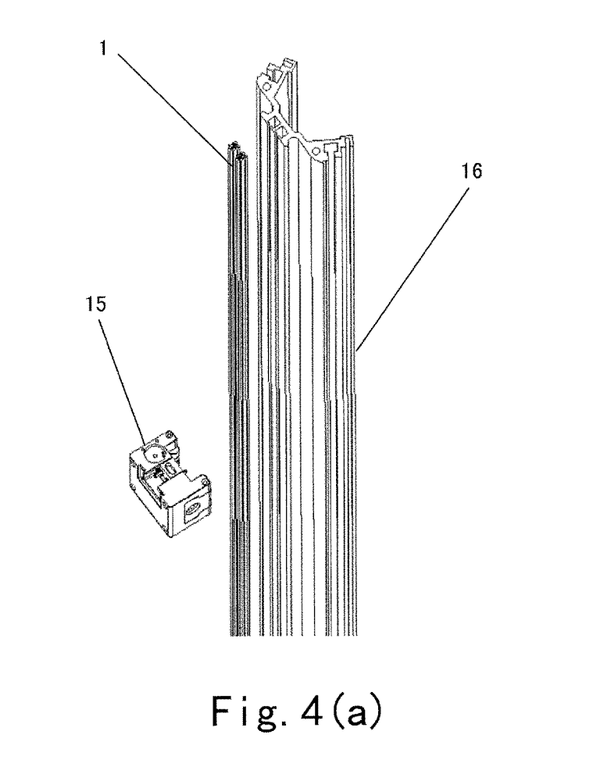

FIG. 4(a) shows an exploded three-dimensional view for a relay module 15, a bus 1 and a pendant cabinet 16 of an embodiment of the present invention. FIG. 4(b) shows an exploded top view for a relay module 15, a bus 1 and a pendant cabinet 16 of an embodiment of the present invention.

Preferably, as shown in FIG. 4(b), the relay module 15 comprises a relay module mechanical interface 151 and a relay module electrical interface 152 for connecting with the cabinet mechanical interface 161 and the cabinet electrical interface on the pendant cabinet 16, respectively.

The relay module electrical interface 152 can be used as the electrical interface of the bus 1 to various attachments (i.e., the movable component) which carry control or signal transmission, and can be used for connecting the input conversion interface 31 and the bus 1, or for connecting the output conversion interface and the bus 1, thereby ensuring the medical pendant system to realize smooth electrical connection. Meanwhile, the relay module mechanical interface 151 ensures that various attachments can be adjusted at any position in lengthwise direction.

Preferably, the relay module 15 located between the movable component and the bus 1 is substantially identical to the relay module 15 located between the execution component and the bus 1, namely, both of them comprise a relay module mechanical interface 151 and a relay module electrical interface 152 for connecting with the cabinet mechanical interface 161 and the cabinet electrical interface on the pendant cabinet 16, respectively. Here, "substantially identical" refers to the both the relay modules 15 comprise the relay module mechanical interface 151 and the relay module electrical interface 152, but they can comprise other different additional structures or parts.

Preferably, as shown in FIG. 4(b), the relay module mechanical interface 151 comprises a convex curved surface portion disposed on the relay module 15, and the cabinet mechanical interface 161 comprises a corresponding concave curved surface portion disposed on the pendant cabinet 16. Although the examples given above only describe the circumstance of the matching of the concave curved surface portion of the pendant cabinet to the convex curved surface portion of the relay module mechanical interface, a person skilled in the art should understand, on the basis of the present invention, that the form of matching of the convex curved surface portion of the pendant cabinet to the concave curved surface portion of the relay module mechanical interface can also be used. Such variation also falls into the protection scope of the present invention.

Preferably, as shown in FIG. 4(b), the relay module electrical interface 152 comprises a pin disposed on the relay module 15, and the cabinet electrical interface comprises a bus 1 disposed on the pendant cabinet 16.

Certainly, a person skilled in the art should understand, on the basis of the present invention, that the relay module electrical interface of the present invention is not limited to a pin, and other forms such as tab, wiring, quick connector, welding, and wireless connection and the like can also be used. Various forms of relay module electrical interfaces fall into the protection scope of the present invention so long as they can realize the effective electrical connection of the relay module and the pendant cabinet.

Figure 5A:
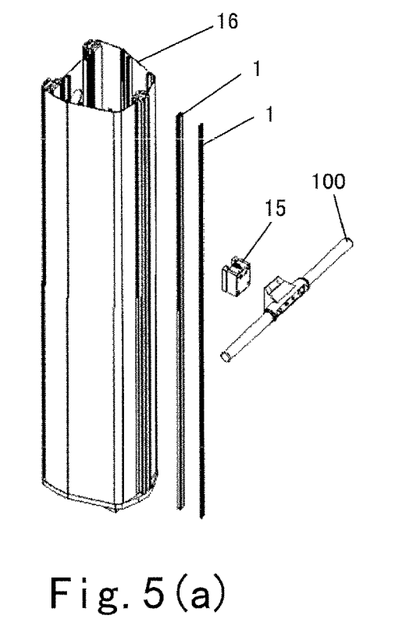
FIG. 5(a) is an exploded three-dimensional view for the movable component, relay module, bus and pendant cabinet of an embodiment of the present invention.
Figure 5B:
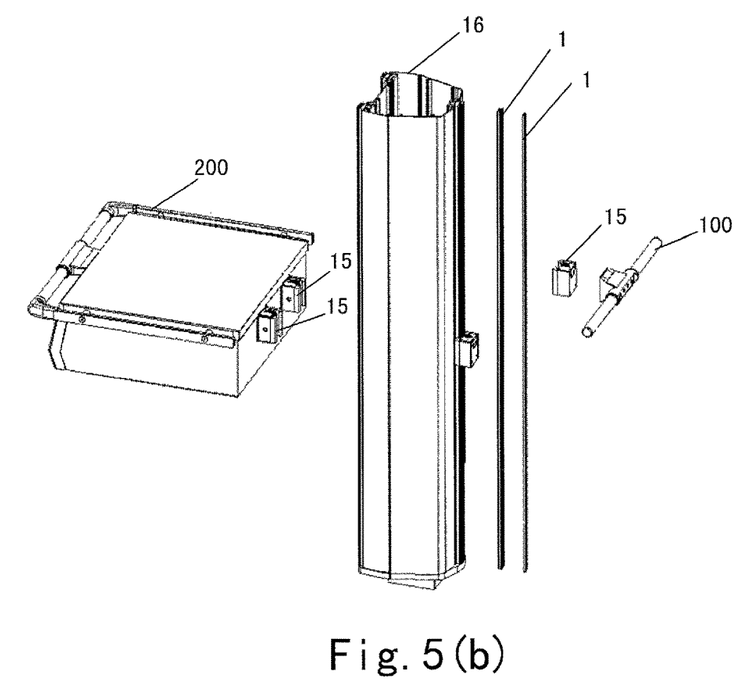
FIG. 5(b) is an exploded three-dimensional view for the movable component, relay module, bus and pendant cabinet of another embodiment of the present invention.

FIG. 5(a) shows an exploded three-dimensional view for a movable component, a relay module 15, a bus 1 and a pendant cabinet 16 of an embodiment of the present invention. FIG. 5(b) shows an exploded three-dimensional view for a movable component, a relay module 15, a bus 1 and a pendant cabinet 16 of another embodiment of the present invention.

As shown in FIG. 5(a), the movable component can be in the form of handle 100. As shown in FIG. 5(b), the movable component can comprise the handle 100 and a laminate 200. Certainly, a person skilled in the art should understand, on the basis of the present invention, that other forms of movable components, such as an infusion rod, a display support arm, a medical guide rail and the like can also be used. The attachments, so long as they can be adjusted at a position in lengthwise direction and can transmit digital or electrical signals, all belong to the so-called "movable component" of the present invention and fall into the protection scope of the present invention.

Figure 6A:
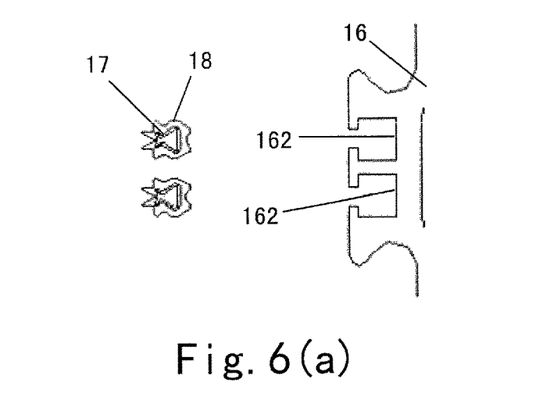
FIG. 6(a) is a cross section for the bus and cabinet of an embodiment of the present invention, in which the bus is not installed to the cabinet yet.
Figure 6B:
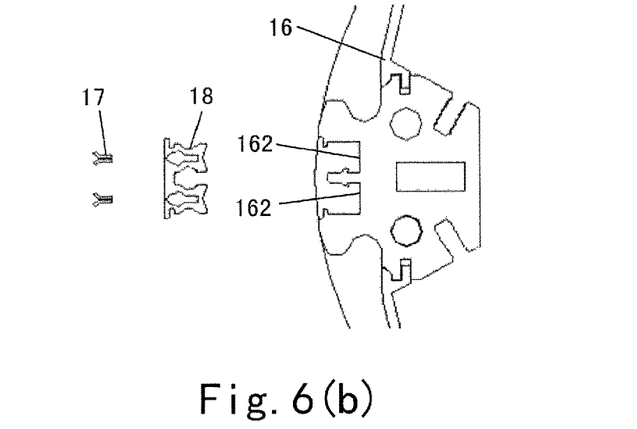
FIG. 6(b) is a cross section for the bus and cabinet of another embodiment of the present invention, in which the bus is not installed to the cabinet yet.
Figure 6C:
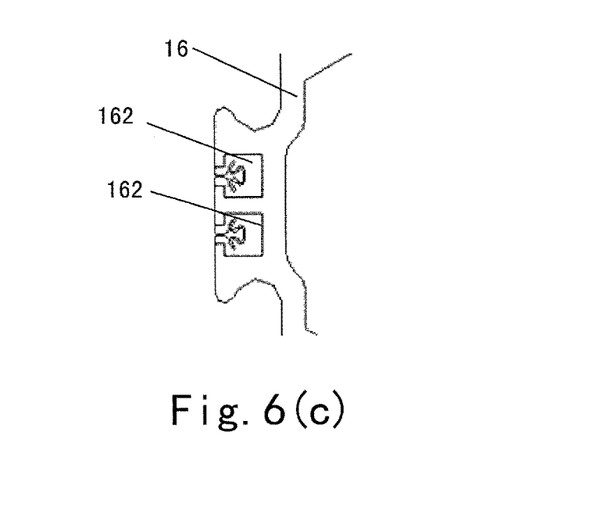
FIG. 6(c) is a cross section for the bus and cabinet of another embodiment of the present invention, in which the bus has been installed to the cabinet.

FIG. 6(a) shows the bus and cabinet of an embodiment of the present invention, in which the bus is not installed to the cabinet yet. FIG. 6(b) shows the bus and cabinet of another embodiment of the present invention, in which the bus is not installed to the cabinet yet. FIG. 6(c) shows the bus and cabinet of another embodiment of the present invention, in which the bus has been installed to the cabinet yet.

Preferably, as shown in FIGS. 6(a)-6(c), the bus 1 is disposed in an inner groove 162 inside the pendant cabinet 16 or on the exterior surface thereof and extending along the lengthwise direction of the pendant cabinet, and the bus 1 comprises an insulator 18 accommodated inside the inner groove 162, and a conductor 17 enclosed inside the insulator 18.

Preferably, the pendant cabinet 16 is at least partially molded via extrusion so as to integrally form the inner groove 162.

Preferably, as shown in FIGS. 6(a)-6(c), the inner groove 162 is substantially filled when the insulator 18 is accommodated inside the inner groove 162 and the conductor 17 is enclosed inside the insulator 18.

In this way, the electrical interface has good reliability and insulation performance, effectively preventing the infiltration of water or other cleaning agents during the cleaning process in a hospital.

Preferably, as shown in FIGS. 6(a)-6(c), the number of the lines of bus 1 is two, namely, the bus 1 comprises two insulators 18 accommodated inside the inner groove 162, and two conductors 17 respectively enclosed inside the two insulators 18.

Certainly, on the basis of the present invention, a person skilled in the art should understand that the number of the lines of the bus of the present invention is not limited to two, other numbers such as three, four can also be used. Various numbers of the lines of the bus fall into the protective scope of the present invention, so long as they can achieve the effective transmission of the power supply and instructions.

Preferably, as shown in FIGS. 6(a) and 6(c), the cross section of the conductor 17 can be substantially Ω shaped. As shown in FIG. 6(b), the cross section of the conductor 17 can also be substantially in inverted Y shape. Certainly, a person skilled in the art should understand, on the basis of the present invention, that other cross section shapes of the conductor, such as V-shape, W-shape, C-shape, or T-shape and so on, can also be used, so long as it can ensure the effective connection or contact between the relay module electrical interface (such as pin) and the bus, such variations also fall within the protection scope of the present invention.

In this way, by means of the appropriate settings of the shape and number of the above insulators and conductors, the simple and reliable connection between the pin (or a plug) of the relay module and the conductors inside the pendant cabinet can be achieved.

Preferably, as shown in FIGS. 5(a) and 5(b), the inner groove 162 extends across the entire length of the pendant cabinet 16.

Preferably, as shown in FIGS. 5(a) and 5(b), the insulator 18 extends along the lengthwise direction of the pendant cabinet. Preferably, as shown in FIGS. 5(a) and 5(b), the insulator 18 also extends across the entire length of the pendant cabinet 16.

Preferably, conductor 17 extends along the lengthwise direction of the pendant cabinet. Preferably, the conductor 17 also extends across the entire length of the pendant cabinet 16.

In this way, the medical pendant system of the present invention can freely adjust the position of a medical attachment (i.e., the movable component) across the entire length of the pendant cabinet, and easily and quickly realize the electrical connection and/or the mechanical connection.

Preferably, as shown in FIG. 3, when an extension function is implemented, relay modules 15 may be disposed between the display module 11 and the bus 1, between the display data line module 12 and the bus, between the pulse sensor module 13 and the bus 1, as well as between the pulse diagnostic instrument module 14 and the bus 1. These relay modules 15 can be substantially identical to the relay module 15 located between the movable component and the bus 1 described previously, as well as the relay module 15 located between the execution component and the bus 1.

The present invention has been exemplarily described above in connection with the figures, although the specific implementations of the present invention are not limited to the above embodiments. Various modifications or variations can be made by a person skilled in the art on the premise of without departing from the technical concept of the present invention, and such modifications or variations of course fall within the protection scope of the present invention.

The invention claimed is:

1. A medical pendant system, characterized in that the medical pendant system comprises a movable component, an execution component and a bus; the movable component comprises a key control module; the key control module comprises a braking system control key and a pendant lifting/lowering control key; the execution component comprises an output control part; the output control part is connected respectively with a bus power supply, a pendant motor, and a braking system; the movable component and the execution component are connected respectively to the bus; the bus is used for transmitting power supply, and also used for transmitting instructions from the movable component to the execution component;

wherein the bus is disposed in an inner groove inside the pendant cabinet or on the exterior surface thereof and extends along the lengthwise direction of the pendant cabinet; and wherein the bus comprises only two lines, each of the two lines comprising an insulator accommodated inside the inner groove and a conductor enclosed inside the insulator.

2. The medical pendant system of claim 1, wherein the medical pendant system further comprises a relay module located between the movable component and the bus, and a relay module located between the execution component and the bus.

3. The medical pendant cabinet of claim 1, wherein the inner groove is substantially filled when the insulator is accommodated inside the inner groove and the conductor is enclosed inside the insulator.

4. The medical pendant system of claim 1, wherein the cross section of the conductor is substantially Y-shaped, Ω-shaped, V-shaped, W-shaped, C-shaped, or T-shaped.

5. The medical pendant system of claim 1, wherein the output control part is further connected with a pendant protecting sensor.

6. The medical pendant system of claim 1, wherein the output control part is further connected with a height limiting unit for limiting the lifting and lowering range of the pendant.

7. The medical pendant system of claim 1, wherein the output control part is further connected with a pendant motor power supply.

8. The medical pendant system of claim 1, wherein the movable component further comprises an environmental lamp module.

9. The medical pendant system of claim 1, wherein the movable component further comprises a display module, and the execution component further comprises a display data line module.

10. The medical pendant system of claim 1, wherein the movable component further comprises a pulse sensor module, and the execution component further comprises a pulse diagnostic instrument module.

11. The medical pendant system of claim 1, wherein the key control module further comprises an input conversion interface.

* * * * *